United States Patent [19]
Hussman

[11] Patent Number: 5,782,771
[45] Date of Patent: Jul. 21, 1998

[54] DUAL, FUSED, AND GROOVED OPTICAL LOCALIZATION FIBERS

[76] Inventor: Karl L. Hussman, 81 Orange St., #301, New Haven, Conn. 06510

[21] Appl. No.: 585,789

[22] Filed: Jan. 16, 1996

Related U.S. Application Data

[63] Continuation-in-part of Ser. No. 423,077, Apr. 17, 1995.
[51] Int. Cl.⁶ ........................................................ A61N 5/06
[52] U.S. Cl. .......................... 600/478; 600/342; 600/344; 600/424; 600/476; 606/2
[58] Field of Search .................. 606/2, 3–18; 600/342, 600/344, 407, 424, 476, 478

[56] References Cited

U.S. PATENT DOCUMENTS 5,370,640  12/1994  Kolff ............................................. 606/2

*Primary Examiner*—David M. Shay
*Attorney, Agent, or Firm*—Timothy T. Tyson; Freilich, Hornbaker & Rosen

[57] ABSTRACT

Optical localization fiber embodiments (200, 260, 270, 290, 310, 330, and 350) suitable for preoperative localization of soft tissue lesions by X-ray mammography, CT MRI, ultrasonography or nuclear medicine are provided. In these embodiments at least one hook is carried by an optical fiber for retention in soft tissue. The tip of the optical fiber is visible through the soft tissue when the origin of the optical fiber is attached to a light source. Embodiments include dual hooks (224, 226) attached through a hole (214) in the tip portion (206), a hook (262) fused to the tip (264), a hook (272) glued to the tip (274), a hook (292) held on by a cap (294), a hook (312) screwed into the tip (320), a hook (340) held in a bore in the tip portion (336) by cement, and a hook (358) in a groove (352). A supplemental optical fiber probe (250) provides a method for locating the fibers inside soft tissue.

6 Claims, 8 Drawing Sheets

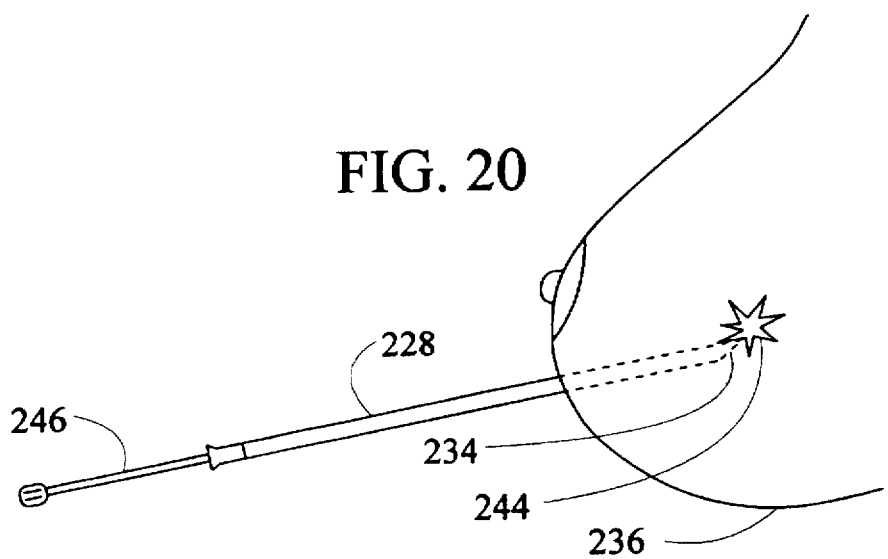
FIG. 20
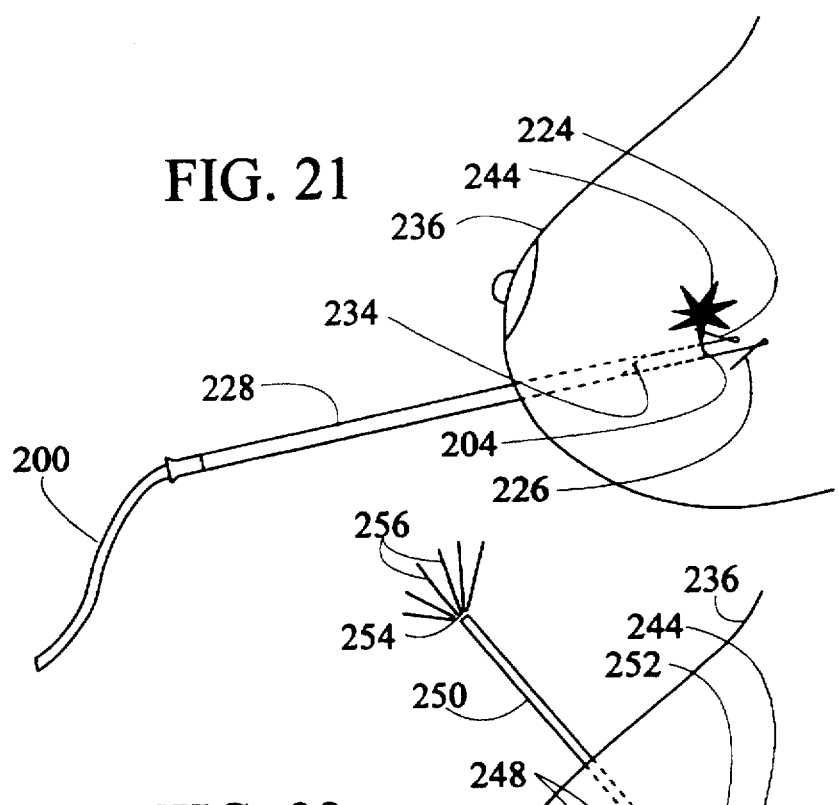
FIG. 21
FIG. 22
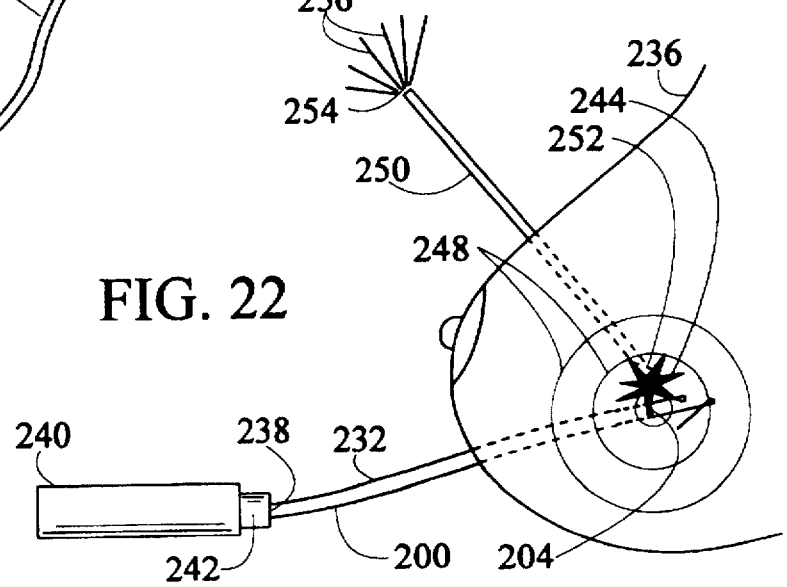

FIG. 28
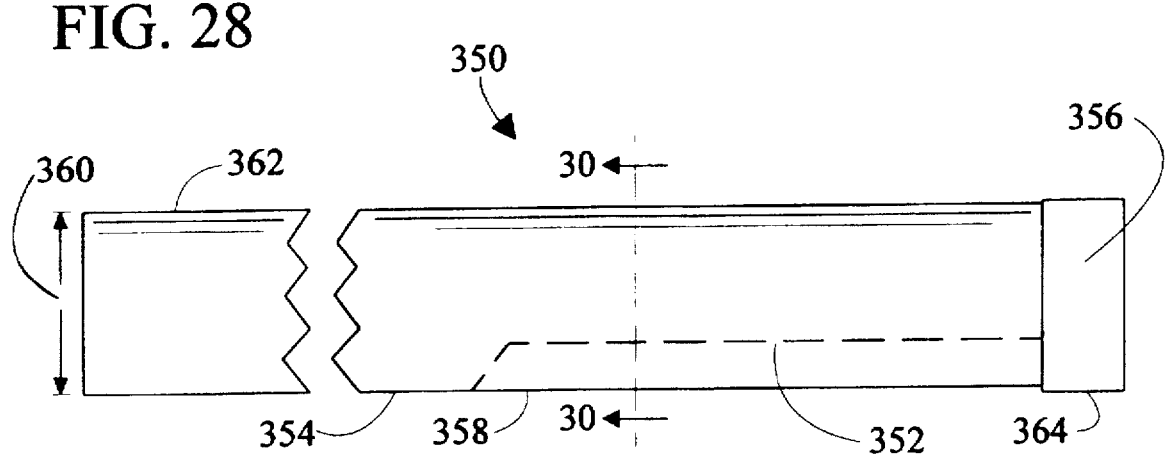
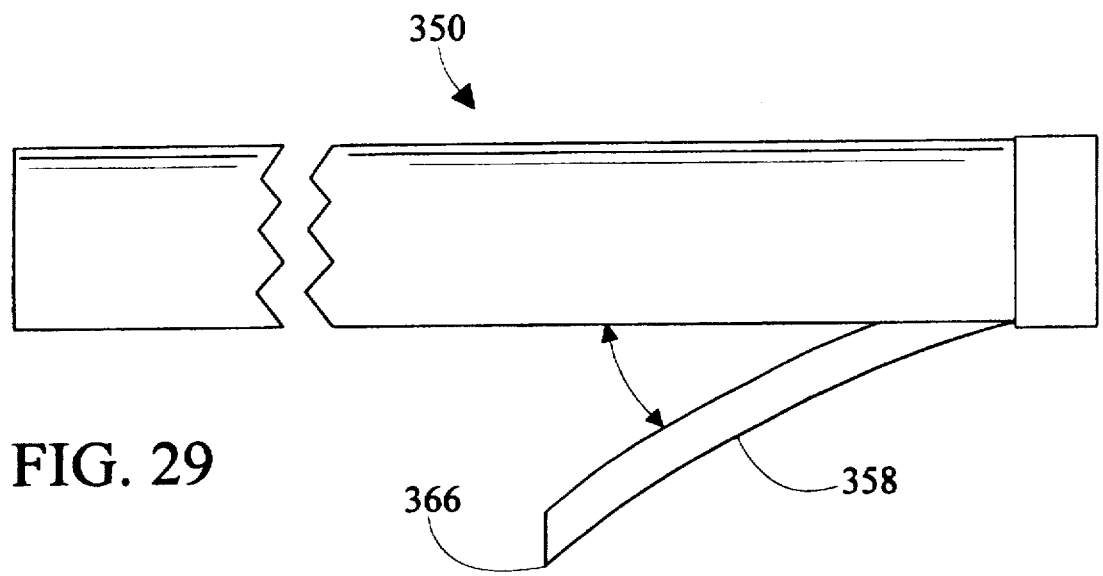
FIG. 29
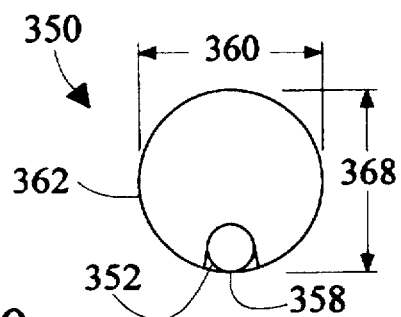
FIG. 30

DUAL, FUSED, AND GROOVED OPTICAL LOCALIZATION FIBERS

CROSS REFERENCE TO RELATED APPLICATION

This is a continuation-in-part of U.S. patent application Ser. No. 08/423,077, filed on Apr. 17, 1995, the contents of which are incorporated herein by reference.

TECHNICAL FIELD

The present invention relates generally to preoperative tissue localization apparatus and more particularly to preoperative breast localization by X-ray radiography, CT ultrasonography, nuclear medicine or magnetic resonance imaging (MRI).

BACKGROUND ART

The current state of the art of preoperative breast tumor localization requires the placement of either a metallic hookwire or a trail of medical grade powdered carbon suspension proximate to the tumor via a localization needle. In the former method, X-ray mammography, ultrasound, or magnetic resonance imaging is used to visualize the lesion in question. The breast is then fixed by compression means, non-compressive immobilization means, or, in the case of ultrasound, manually. A needle is inserted into the breast so that its tip lies proximate to the breast lesion. If carbon localization is used, a trail of carbon is formed from the lesion to the skin surface as the carbon suspension is injected through the needle as the needle is withdrawn. If hookwire localization is used, a fine metallic wire is inserted through the needle. The wire typically is bent or curved at the tip so that it forms a small hook. If the bend is sharp, the hook springs apart as it is passed distal to the tip of the localization needle. In this manner, it becomes substantially fixed at the site of the needle tip. The needle is then withdrawn leaving the hookwire in place. The patient is taken to surgery where the surgeon follows at least part of the carbon trail or hookwire to find the lesion for excision.

Copious references pertaining to the use of hookwires in the imaging literature are available. Literature references include Gallagher, W. J., et al., "Minimal Volume Excision of Nonpalpable Breast Lesions," *American Journal of Radiology*, 153:957, 1989; Czarnecki, D. J., et al., "Toluidine Blue Dye as a Breast Localization Marker," *American Journal of Radiology*, 153:261, 1989; Schoenberger, S. G., et al., "A New Coaxial Needle for Pre-operative Localization for Breast Abnormalities," *British Journal of Radiology*, 64:699–707, 1991; Svane, G., "A Stereotaxic Technique for Preoperative Marking of Non-palpable Breast Lesions," *Acta Radiologica Diagnosis*, 24:145, 1983; Langlois, S. L. P., Carter, M. L., "Carbon Localization of Impalpable Mammographic Abnormalities," *Australian Radiology*, 35:237, 1991; Czarnecki, D. J., et al., "Comparison of the Anchoring Strengths of the Kopans and Hawkins II Needle-hookwire Systems," *Radiology*, 183:573, 1992; D'Orsi, C. J., et al., "Complication Involving a Braided Hookwire Device," *Radiology*, 187:580, 1993; Kopans, D. B. et al., "A Modified Neddle-Hookwire Technique to Simplify Preoperative Localization of Occult Breast Lesions," *Radiology*, 134:781, 1980; Ghiatas, A. A., et al.,"Modified Localization Wire for Breast Lesions," *European Radiology*, 2:266, 1992; Homer, M. J., et al., "Prebiopsy Needle Localization: Methods, Problems and Expected Results," *Radiological Clinics of North America*, 30:139, 1992; Homer, M. J., "Localization of Non-palpable Breast Lesions with the Curved-end, Retractable Wire," *American Journal of Radiology*, 151:919, 1989; Urritia, E. J., et al., "Retractable-barb Needle for Breast Lesion Localization," *Radiology*, 169:845, 1988. References pertaining to transillumination of breast tissue are: Jarlman, O., "Time-resolved Transillumination of the Breast," *Acta Radiologica*, 33:277, 1992; and, Monsees, B., et al., "Light Scanning of Non-palpable Breast Lesions," *Radiology*, 167:352, 1987. A reference pertaining to optical fiber diffuser tips is Malone, D. E., et al., "Sonographic Changes During Hepatic Interstitial Laser Photocoagulation: an investigation of Three Optical Fiber Tips," *Investigative Radiology*, 27:804–813, 1992. The disclosures of the above cited references are hereby incorporated into and liberally drawn from for this background section.

Often the location of the hookwire tip is not readily apparent, and the surgeon must use measurements of the hookwire length, and visual triangulation to help guide him/her. A tugging maneuver is sometimes utilized in order to find the tip since the breast tissue will then move in the locality of the hookwire tip. This maneuver may displace the hookwire tip however. While it is possible to locate the tip of the hookwire fluoroscopically, this method requires a dedicated fluoroscopy suite and radiation protective aprons for all operating room personnel. In addition, unless the fluoroscopic tube can be angled to yield mediolateral and anteroposterior projections, the precise depth of the hookwire cannot be readily ascertained. For these reasons, fluoroscopic guidance is not feasible.

Intraoperative transillumination of the breast with an external light source has been used in conjunction with carbon localization for delineation of the dark carbon trail against the reddish glow of surrounding transilluminated breast tissue.

Both the hookwire and carbon trail methods are cumbersome in actual use. The tip of a hookwire cannot be seen through breast tissue, and the surgeon may have to search for it, commonly necessitating longer operating time, and a larger incision. A carbon trail tends to blacken surrounding tissue if it is cut into by a surgeon. Because of this, it is not always possible to determine the exact end of the trail. Commonly, the carbon trail may become broken if a steady stream of carbon is not injected. A method of localization that is easier to see and requires smaller incisions would offer many advantages.

DISCLOSURE OF INVENTION

The present invention is directed to an optical localization fiber with a hooked tip for preoperative localization of breast lesions identified by X-ray mammography, ultrasound, MRI, or nuclear medicine. The optical fiber enables the surgeon to identify the tip of the optical fiber by the light which preferably originates from a laser connected to the origin of the optical fiber.

The optical fiber has the advantage of allowing continuous and direct visualization of the light emanating through breast tissue from the fiber tip. Smaller breast incisions need be made and smaller amounts of tissue need be removed during breast surgery. In addition, the surgical approach to lesions need not be along the course of the localizing optical fiber, since radiant light emanating from the site of the lesion may be seen from any perspective.

Apparatus in accordance with the invention are characterized by an optical fiber of a diameter which allows passage through a localization needle, a hook or curve to allow retention in a breast substantially without displacement, and a tip which allows diffusion of transmitted light for visualization through breast tissue by the surgeon.

In accordance with a preferred embodiment, the optical fiber tip has a hole for attachment of a dual hook assembly therethrough.

In accordance with another preferred embodiment, the optical fiber tip is fused to a hook.

In accordance with another preferred embodiment, the optical fiber tip is cemented to a hook.

In accordance with another preferred embodiment, the base of a hook has a plurality of bends and is retained on the optical fiber tip by a molded cap.

In accordance with another preferred embodiment, the optical fiber has a tapped tip portion that receives the screw portion of the base of a hook.

In accordance with another preferred embodiment, the optical fiber has a tip portion that is end drilled for receiving the base of a hook.

In accordance with another preferred embodiment, the optical fiber tip portion is grooved for retention of a hook within the diameter of the fiber shaft.

In accordance with an important aspect of the invention, an optical fiber probe allows location of the optical fiber tip deep within tissue.

All embodiments may be used in combination with carbon marking of the lesion site to facilitate visualization of the region to be surgically excised.

The novel features of the invention are set forth with particularity in the appended claims. The invention will best be understood from the following description when read in conjunction with the accompanying drawings.

BRIEF DESCRIPTION OF DRAWINGS

FIG. 20 is a perspective view of a breast with a needle positioned proximate to a breast lesion;

FIG. 21 is a perspective view of a breast with a dual hook optical localization fiber engaged proximate to a breast lesion which has been focally marked with a powdered carbon solution;

FIG. 22 is a perspective view of a breast with a dual hook optical localization fiber connected to a light source while engaged proximate to a breast lesion which has been focally marked with a powdered carbon solution;

FIG. 28 is a side view of a grooved optical localization in the closed position;

FIG. 29 is a side view of a grooved optical localization fiber in the open position; and, FIG. 30 is a cross sectional view of a grooved optical localization fiber along the line 30—30 of FIG. 28.

BEST MODES FOR CARRYING OUT THE INVENTION

Figure 1:
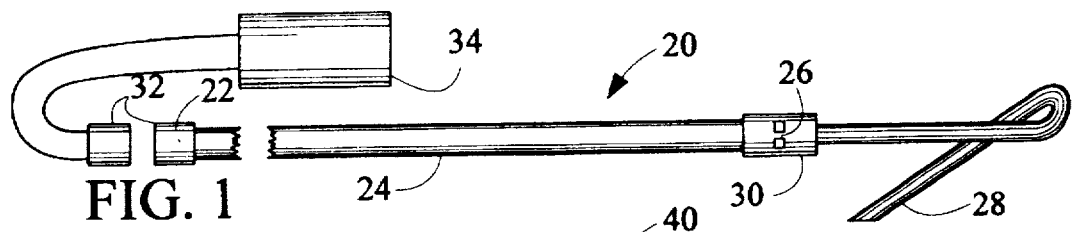
FIG. 1 a side view of a diffusing optical localization fiber in accordance with the present invention.
Figure 11:
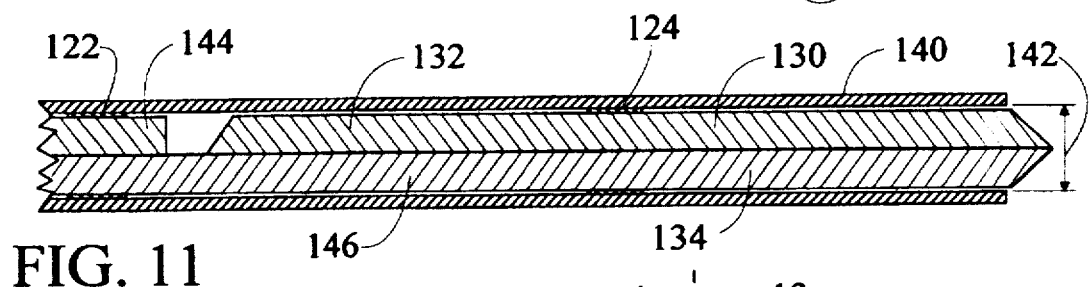
FIG. 11 is an enlarged cross sectional side view of a pincher hook optical localization fiber within a localization needle.

FIG. 1 illustrates a side view of a diffusing optical localization fiber 20 in accordance with the present invention having an origin 22, a shaft 24, and an optical fiber tip 26. A metallic or plastic hook 28 is bound to the tip by means of a connection 30. The hook has a spring action to engage in tissue once the localization needle is withdrawn. A sectional view of a localization needle with an optical fiber inside prior to insertion is shown in FIG. 11. Radiant light emanating from the localization fiber tip may be diffused by the connector 30 if it is made of a translucent material such as plastic, quartz, or ground glass. Alternatively, the connector 30 may be opaque, but fenestrated to allow light to emanate from the optical fiber tip 26. A coupler 32 is located at the origin 22 of the diffusing optical localization fiber 20 to unite with a laser or other light source 34.

Figure 2:
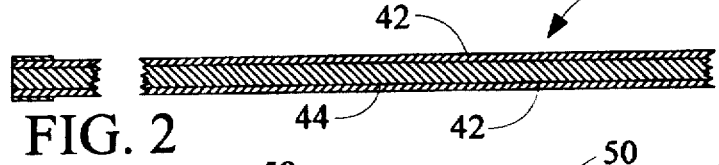
FIG. 2 is a longitudinal cross sectional view of an optical localization fiber with a cladding or coating.

FIG. 2 illustrates a longitudinal cross sectional view of an optical fiber 40 with cladding and/or coating 42 along the shaft 44.

Figure 3:
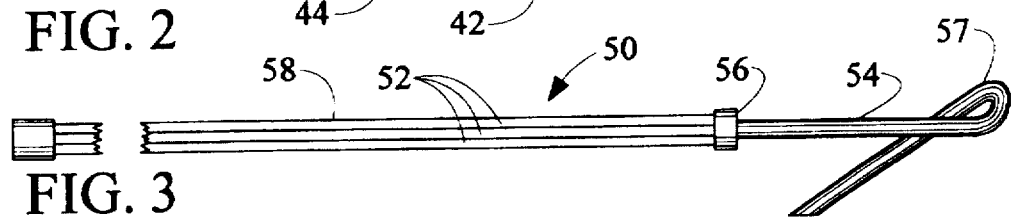
FIG. 3 is a side view of a bundled optical localization fiber.

FIG. 3 illustrates a bundled optical localization fiber 50 with individual fibers 52. A metal or plastic hook 54 is affixed to the tip of the fiber bundle and arises from a small metallic or plastic fastener 56 bound to the tip of the bundled optical localization fiber 50 either by adhesive, integration with the cladding and/or coating 58 (not shown here), or by a variety of other conceivable means. The hook 54 may have the form of a smooth curve or of a sharp bend 57 and may be fashioned from stainless steel including high nickel content stainless, titanium, nitinol, or a variety of other metals including those which cause low artifact during magnetic resonance imaging. Hooks with either a smooth curve or sharp bend have a spring action which allows them to be inserted through a localization needle such as the localization needle of FIG. 11. Both types of hooks snag tissue, preventing displacement when the localization needle is withdrawn. The bundled optical localization fiber 50 preferable has a diameter allowing insertion through a 14 through 22 gauge needle, although the preferred diameter is 20 gauge.

Figure 4:
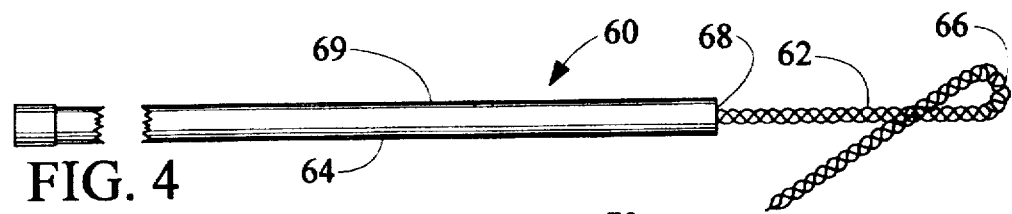
FIG. 4 is a side view of a hybrid optical localization fiber joined to a spiral wire along its shaft.

FIG. 4 illustrates a hybrid optical localization fiber 60 with a spiral metallic wire 62 extending down the shaft 64. The spiral metallic wire 62 forms a braided metallic hook 66 past the optical fiber tip 68. Cladding and/or coating 69 prevents unravelling of the spiral metallic wire.

Figure 5:
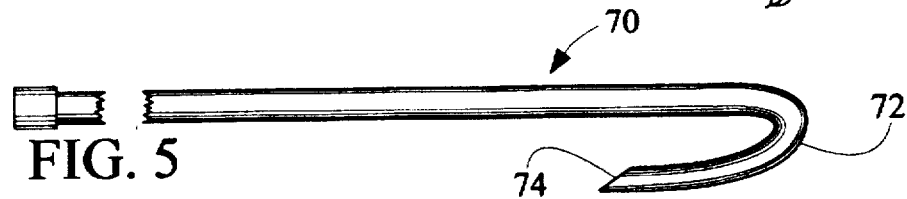
FIG. 5 is a side view of a single composition optical localization, fiber.

FIG. 5 illustrates a single composition optical localization fiber 70. The optical fiber hook 72 is molded from the optical fiber itself, and is resilient allowing passage of the optical localization fiber 70 through a needle. The fiber 70 curves as the optical fiber tip 74 emerges from a needle. The bundled optical localization fiber 50 (FIG. 3) may be molded to form a similar curve. The optical fiber hook has a point to penetrate breast tissue and thereby facilitate retention.

Figure 6:
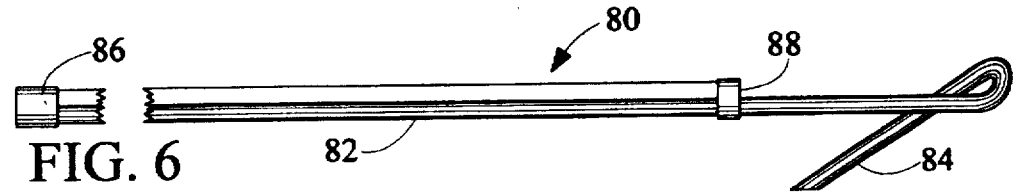
FIG. 6 is a side view of a tandem optical localization fiber.

FIG. 6 illustrates a tandem hookwire-optical localization fiber 80. A longitudinal wire 82 runs down the shaft of the fiber optical on the surface, totally beneath the surface, partially beneath the surface, outside a coating, inside a coating, on the surface of bundled optical fibers, or within bundled optical fibers. The longitudinal wire 82 is continuous with a metallic hook 84 and is held on the optical fiber or fibers 80 by fasteners 86 and 88.

Figure 7:
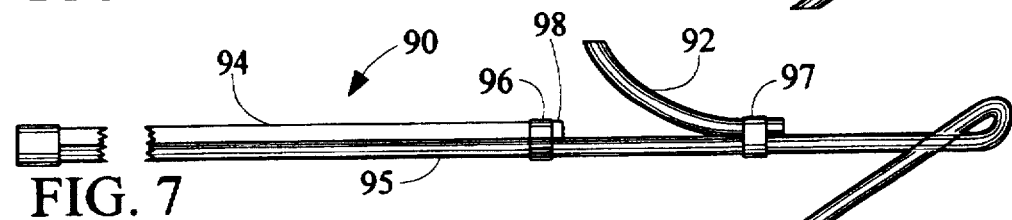
FIG. 7 is side view of a multi-hook optical localization fiber.

FIG. 7 illustrates a multi-hook optical localization fiber 90. A variety of possible configurations, orientations, and positions of a plurality of hooks can readily be envisioned all of which are intended to be represented by this generic illustration. For example, a second hook 92 is shown. Since this hook and similar hooks are inside the combination of the diameters of the fiber optic 94 and longitudinal wire 95, no increase in needle diameter is necessary. The entire localization wire may be metallic without an optical fiber component. Fasteners 96 and 97 are positioned at the optical fiber tip 98 and around the second hook 92, respectively.

Figure 8:
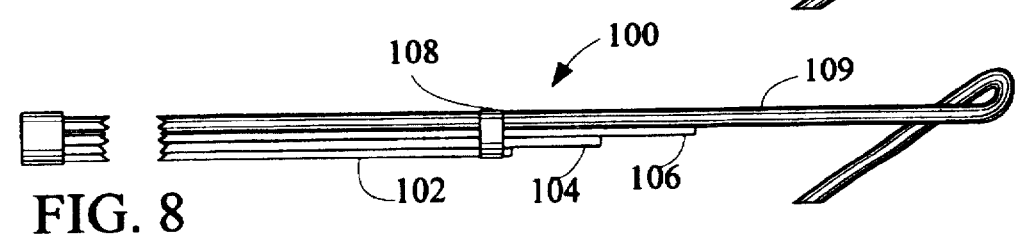
FIG. 8 is a side view of a staggered optical localization fiber.

FIG. 8 illustrates a staggered optical localization fiber bundle 100 with a plurality of staggered optical fibers 102, 104, and 106. A fastener 108 secures a plastic or metallic hook 109.

Figure 9:
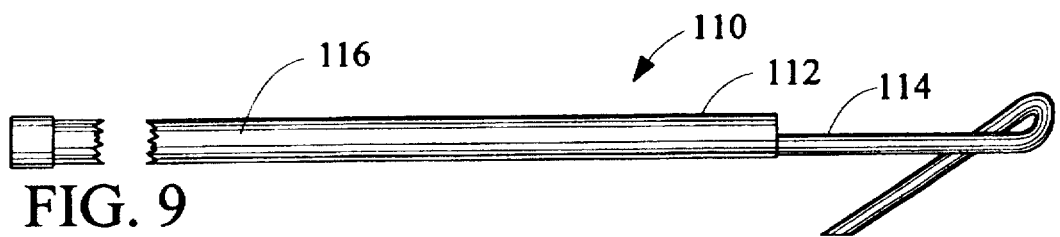
FIG. 9 is a side view of a coated tandem optical localization fiber.

FIG. 9 illustrates a coated tandem hookwire-optical localization fiber 110. No fastener is necessary since the cladding and/or coating 112 holds the wire 114 and shaft 116 together.

Figure 10:
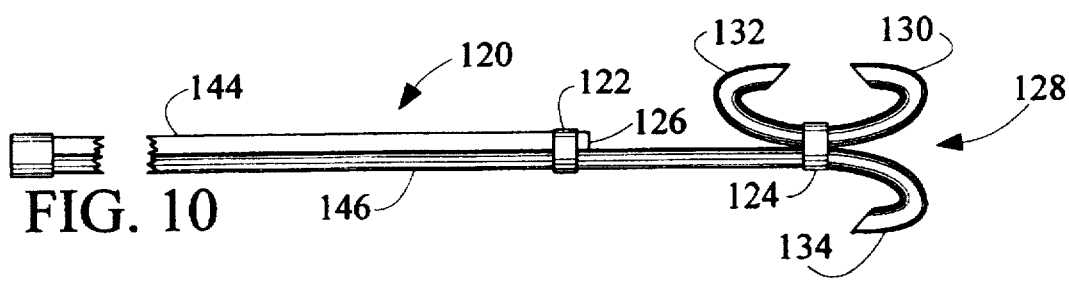
FIG. 10 is a side view of a pincher hook optical localization fiber.

FIG. 10 illustrates a pincher-hook optical localization fiber 120. Fasteners 122 and 124 are positioned at the optical fiber tip 126 and around a triple hook 128, respectively, comprising a distal pincher hook 130, a proximal pincher hook 132, and a curved metallic hook 134. Since all hooks have a gentle curve, they may be inserted into the breast localization needle 140 shown in FIG. 11 inside an internal diameter 142 approximately equal to the sum of the diameters of the optical fiber 144 and wire 146. This is illustrated in FIG. 11.

FIG. 11 is an enlarged cross sectional view illustrating the pincher-hook optical localization fiber 120 within the shaft of a needle 140. The needle is inserted into the tissue proximate to the lesion. The pincher-hook optical localization fiber 120 is held in position as the needle 140 is withdrawn thereby releasing the hooks 130, 132, and 134 to engage tissue immobilizing the optical fiber 144.

Figure 12:
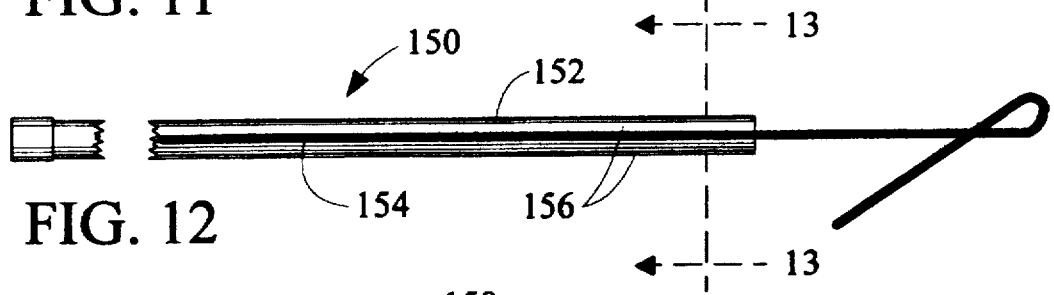
FIG. 12 is a side view of a rosette optical localization fiber bundle with the rear side fibers omitted.

FIG. 12 illustrates a side view of a rosette optical localization fiber bundle 150 with the near side fibers omitted.

The bundle also has cladding and/or coating 152, a central wire 154 surrounded by a multiplicity of optical fiber shafts 156 which may be bound to the central wire and each other by adhesive.

Figure 13:
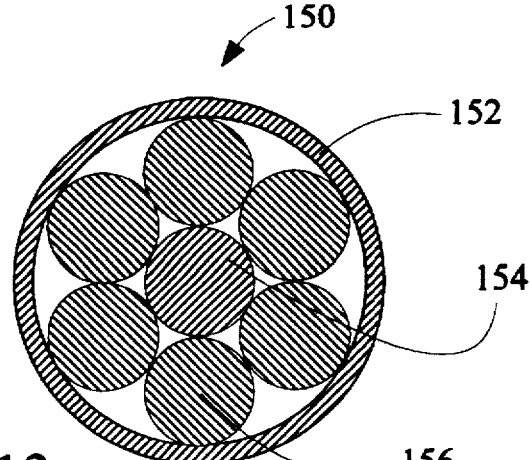
FIG. 13, is a cross sectional view along the line 13—13 with all the optical fibers in place of FIG. 8.

FIG. 13 is an enlarged cross sectional view along line 13—13 of FIG. 12 with the optical fibers in place showing optical fiber shafts 156 arranged in a rosette pattern about the central wire 154. Coating and/or cladding 152 encases the optical fibers and wire.

Figure 14:
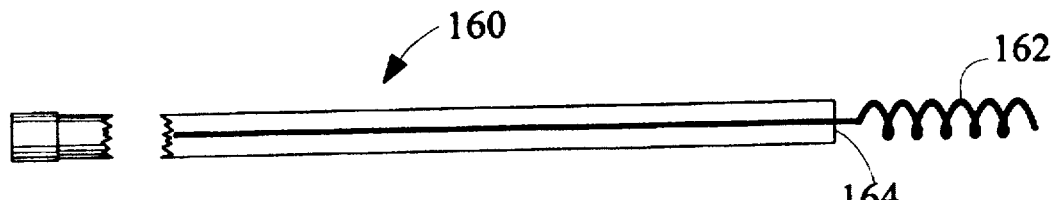
FIG. 14 is a side view of a helical optical localization fiber.

FIG. 14 is a side view of a helical optical localization fiber 160 with a plastic and/or metallic helix 162 at the optical fiber tip 164.

Figure 15:
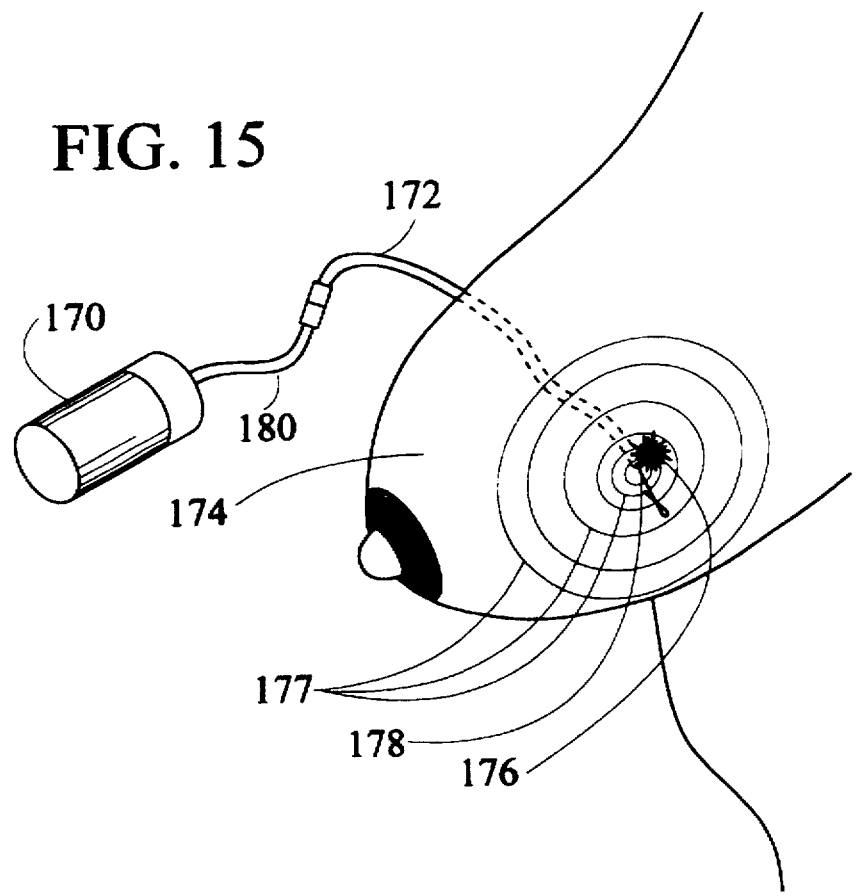
FIG. 15 is a perspective view of a breast with a single composition optical localization fiber hooked proximate to a breast lesion, with light radiating from the tip of the hook.

FIG. 15 demonstrates a laser or other light source 170 coupled to an optical localization fiber 172 within a breast 174 proximate to a lesion 176. The amount of light represented by the concentric circles 177 radiating from the optical fiber tip 178 may be adjusted by changing the laser output. A variety of light sources and wavelengths may be used, such as a high output light emitting diode or a quartz-halogen bulb with a suitable optical fiber connector 180. Pulsed lasers or light sources with a stroboscopic effect may be used to enhance output at the tip 178. The lesion 176 is dark to illustrate powdered carbon which may be injected at the site of the lesion 176. The method of providing medical grade powdered carbon solution in combination with an optical localization fiber for placement at the site of a tissue lesion allows visualization of the lesion, which will be dark because of the carbon, through breast or other tissue as the optical fiber transmits light. In this preferred method of lesion localization, a localizing needle tip is positioned proximate to a lesion via a variety of known stereotactic procedures including X-ray mammography, ultrasound, nuclear medicine, or magnetic resonance imaging (MRI). Approximately 0.1 to 0.3 cubic centimeters of a 4% or other injectable concentration of sterile medical grade carbon solution is injected at this location, similar to the known technique of methylene blue injection for preoperative marking of lesions. Although methylene blue diffuses, carbon does not diffuse, and surgery may be scheduled electively following localization.

After the carbon is instilled, the optical localization fiber is passed through the needle 140, and engaged into tissue. The needle is removed, and the localization fiber is left in place. At surgery, a skin incision is made at any desired location. The optical fiber is activated, thus transilluminating the breast. The carbon is identified as a dark spot, surrounded by illuminated tissue, guiding the surgeon to the lesion. The optical localization fiber may be used without carbon, however.

Svane introduced carbon trail localization in 1978 and has performed the procedure in 1800 cases with no complications to date. Langlois reported the use of carbon trail localization in 53 patients (but has since used it on over 400 patients without any adverse effects identified) and found it to be "highly acceptable to patients, referring clinicians and radiology staff." These researchers considered medical grade carbon so inert that it may be left permanently within the breast "as for example when a biopsy result is unequivocally benign."

Medical grade powdered carbon suspension may be prepared in a variety of ways by those skilled in the art of pharmacy. For example, Norit C extra medicinal activated charcoal which complies with BPC/USP requirements. The raw material has been tested for: identification, acidity/alkalinity, acid soluble substances, water soluble substances, tarry matter, higher aromatic hydrocarbons, copper, lead, zinc, arsenic, chloride, sulphate, cyanogen compounds, sulphide, loss on drying, sulphated ash, and microbial limits.

The inventor has had this type of carbon heated to 800 degrees centigrade by High Temperature Calibration of Signal Hill, Calif., and analyzed with a non-heated sample for control, in order to determine the presence of any potentially carcinogenic physiologically active aromatic hydrocarbons, i.e. ¾ benzpyrene and related carcinogens by S&N Labs of Santa Anna, Calif. Each sample was extracted for 48 hours using a Soxhlet extractor. A portion of each sample was spiked with a surrogate mixture, according to Environmental Protection Agency (EPA) procedure 8310. Analysis of the spiked surrogates in the samples revealed no recovery of these related compounds. This indicates that the sample materials have a strong affinity for polynuclear aromatics (PNAs) and will not normally permit their extraction and quantification. This suggests that under physiologic conditions no PNA is expected to be released into the body, and in fact, there is a high affinity of the carbon for trace amounts of these substances within the body, so that the material may remove them from fluids which it contacts. Therefore, heating the carbon is probably not necessary for purposes of PNA pyrolysis, however, heating destroys small traces of endotoxin within the carbon.

The steps of manufacturing the carbon suspension include measuring a volume of physiologically iso or hypotonic sodium chloride solution, adding the appropriate amount of powdered carbon to the saline solution to yield the desired weight/volume (w/v) concentration, adding the resulting mixture to containers of a desired size, sealing the containers and autoclaving the containers. For example, 4 grams of medicinal grade powdered carbon solution may be added to 100 milliliters of 0.9% sodium chloride to yield a 4% w/v concentration. If desired, the step of heating the carbon powder to remove all endotoxins may be performed. Any concentration may be used as long as it is injectable through a localization needle.

To the inventor's knowledge, the method and advantages of focal carbon marking of a breast lesion in combination with insertion of a hookwire proximate to the lesion as described throughout this disclosure has not been taught in the scientific literature and has not been claimed as intellectual property. On the contrary, the use of carbon for formation of a "trail" has been taught by the cited references as a means of avoiding the use of a hookwire.

It should be clear that any feature of any embodiment described herein may readily be combined, altered, or rearranged in innumerable variations. For example, features of FIG. 1 and FIG. 10 may be combined and altered to yield FIG. 16, a dual hook optical localization fiber 200 having a dual hookwire means 202 for retaining the tip 204 where desired. In this embodiment, the tip portion 206 of the fiber is narrowed bilaterally to create two substantially planar sides 208, 210 for accommodating the thicknesses of the wire 212 of the dual hookwire assembly 202. The wire 212 is threaded through a hole 214 traversing the resulting short axis of the tip portion 206 to retain the hookwire assembly 202. The planar sides 208, 210 are substantially perpendicular to the hole and are substantially parallel to each other and extend from the hole 214 to the tip 204. The diameter of the hole 214 is equal to or slightly greater than the diameter of the wire 212. The wire 212 has bends 216, 218 immediately outside the hole 214 and first and second portions 220, 222 which are substantially parallel to each other. The first proximal hook 224 and second distal hook 226 are fashioned at each of the free ends of the wire with the first hook coupled to the first portion of the wire and the second hook coupled to the second portion or the wire. These hooks are slightly staggered so that they may both lie in juxtaposition within the bore of a localization needle 228 (FIGS. 20–22) with the second hook 226 spaced further from the tip 204 than the first hook 224. Because the tip portion 206 has been narrowed, the total distance across the tip portion 206 and the first and second portions 220, 222 of the wire 212 is approximately equal to the diameter 230 of the main body of the fiber shaft 232. If desired, a single hook may be used, although this arrangement is less advantageous.

Figure 16:
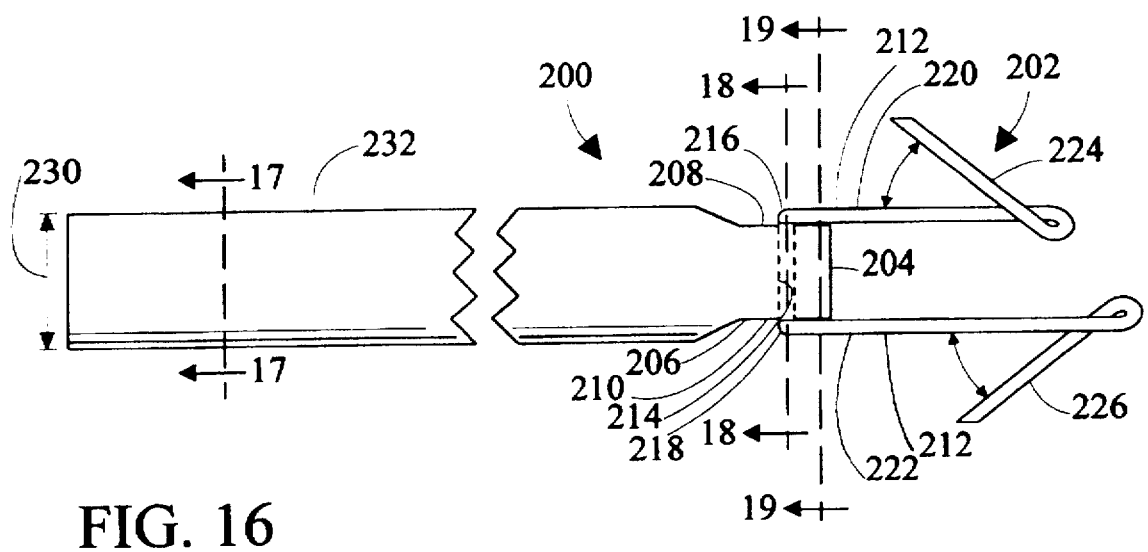
FIG. 16 is a side elevational view of a dual hook optical localization fiber.
Figure 17:
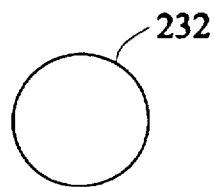
FIG. 17 is a cross sectional view along line 17—17 of FIG. 16.
Figure 18:
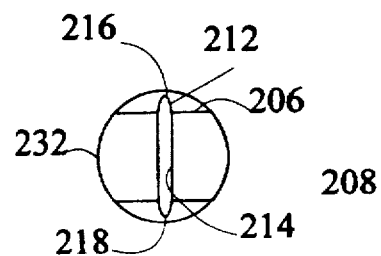
FIG. 18 is a cross sectional view along line 18—18 of FIG. 16.
Figure 19:
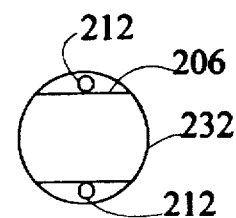
FIG. 19 is a cross sectional view along line 19—19 of FIG. 16.

FIG. 17 shows a cross section of the main body portion of the fiber shaft 232 along the line 17—17 of FIG. 16 illustrating that the cross section is preferably circular. FIG. 18 shows a cross section through the hole 214 along line 18—18 of FIG. 16. FIG. 19 shows a cross section through the tip portion 206 along line 19—19 of FIG. 16. The wire 212 has bends 216, 218 immediately outside the hole 214. The optimal narrowing of the main body of the fiber shaft 232 to each of the planar sides 208, 210 is approximately equal to the diameter of the wire 212. For example, if the diameter of the wire 212 is 0.2794 millimeter (0.011 inch), the fiber shaft 232 is narrowed at the tip portion 206 by at least 0.5588 mm (0.022 inch). Obviously, this necessitates the use of a fiber shaft 232 of a greater diameter than this. In order to assure that the dual hook assembly 202 does not break free from the tip portion 206, the tip portion must have adequate thickness. A standard optical fiber diameter is 1000 microns or 1 mm (0.03937 inch). The inner diameter of an extra thin wall 17 gauge needle is 1.27 mm (0.050 inch). The tip portion 206, therefore, is preferably slightly less than 1.27 mm–0.5588 mm=0.7112 mm (0.050 inch–0.022 inch= 0.028 inch). In order to allow for slight variations in the wire 212, fiber shaft 232, internal needle diameter, the thickness of the tip portion 206 allows a little tolerance and is preferably 0.635 mm (0.025 inch). This thickness is adequate to prevent detachment of the dual hook assembly 202 from the tip portion 206 due to fragmentation of the tip portion 206 during moderate torquing and longitudinal stressing of the dual hook assembly 202. Obviously, larger fiber shaft 232 diameters could be used, however, a larger needle gauge would then be required as well. The use of 0.3048 mm (0.012 inch) stainless steel wire results in a slightly thinner tip portion 206, but provides greater anchoring strength in tissue. The presence of the two hooks 224 and 226 substantially increases anchoring strength compared to localization wires having a single hook.

In order to document the validity of the invention disclosed herein, the inventor constructed several dual hook optical localization fibers 200 each using the following materials: a 25.4 centimeter (10 inch) length of a single filament 1000 micron (1 mm) diameter unjacketed communications grade light guide, such as stock number E2564 light guide sold by Edmund Scientific Co. of Barrington, N.J.; a 10.16 cm (4 inch) length of a 0.02794 mm (0.011 inch) diameter type 304V stainless steel wire, such as stock number K-SWGX-110 wire sold by Small Parts Inc. of Miami Lakes, Fla.; and a 15.24 cm (6 inch) length of extra thin wall 17 gauge type 304 stainless steel tubing, such as stock number K-HTX-17XTW tubing, also sold by Small Parts Inc. The tip portion 206 was symmetrically sanded flat on opposing sides for a length of approximately 2 mm yielding a thickness of approximately 0.635 mm (0.025 inch). A 1.27 cm (½ inch) length of the wire 212 was used as a bit, the wire was cut at an angle to create a sharp tip, and the hole 214 was drilled through the short axis of the tip portion 206. The wire 212 was passed through the hole 214. Using needle nose pliers, two staggered hooks 224 and 226 were fashioned, and the excess wire snipped off.

As shown in FIG. 20, a needle tip 234 was created by sanding the end of a 17 gauge tube 228. The needle 228 was then passed into a human breast mastectomy specimen 236 weighing 1800 grams. The dual hook optical localization fiber 200 was inserted into the needle 228 as shown in FIG. 21. The hooks 224 and 226 were engaged, and the needle 228 completely withdrawn over the fiber 200 as shown in FIG. 22. The bare origin 238 of the fiber 200 was connected to a 15 milliwatt laser module 240 having a 635 nanometer wavelength with a fiber optic connector 242 such as a laser sold as part number PM12(635-15)F4 by Power Technology, Inc. of Little Rock, Ark. The sanded tip portion 206 acted as a diffuser tip. The light emanating from the tip portion 206 and tip 204 was easily visible through several centimeters of tissue when the laser was activated.

The method of breast lesion localization using the dual hook optical localization fiber 200 proceeds as follows using the same FIGS. 20–22. After a lesion 244 is detected by medical imaging and the breast is substantially immobilized, the needle 228 is inserted into the breast 236 to the site of the lesion 244 as shown in the perspective view of the breast shown in FIG. 20. A stylet 246 is shown to be partially removed from the needle 228. The tip of the stylet is within the shaft of the needle and is not shown. The needle tip 234 is positioned proximate to the lesion 244.

FIG. 21 illustrates engagement of the hooks 224, 226 of the dual optical localization fiber 200 after complete removal of the stylet 246 (FIG. 20) and insertion of the fiber 200 past the needle tip 234 followed by partial withdrawal of the needle 228 from the breast 236 allowing the hooks to spring out. If desired, instillation of a small amount (0.1–0.4 milliliter) of 4% medical grade powdered carbon suspension in saline or any other appropriate injectable concentration may be injected through the needle 228 prior to insertion of the fiber 200 in order to mark the lesion 244 for easier identification by the surgeon. Any appropriate volume may be injected. The lesion 244 in FIG. 21 is shown to be darkened by such carbon particles.

FIG. 22 is a perspective view of the breast 236 with the retained dual hook optical localization fiber 200 after total removal of the needle over the fiber shaft 232 and connection of the origin 238 to a laser or other light source 240 via an optical fiber connector 242. Concentric lines 248 indicate illumination of the fiber tip 204, which may be visualized through the tissue.

This figure also illustrates a method for initially helping to locate the tip 204. A rigid optical fiber probe 250 having a sharp probe tip 252 and an indicator end 254 is utilized. The indicator end 254 may simply be the bare end of a single optical fiber or light guide or an optical fiber bundle. In order to further determine the location of the fiber tip 204 deep within the breast 236 in those cases where it is difficult to see the light emanating through tissue, the probe 250 is inserted into the breast to the expected location of the fiber tip 204. The fiber 200 is simultaneously illuminated by the laser or other light source 240. When the probe tip 252 is proximate to the fiber tip 204, the indicator end 254 will emanate light represented by the lines 256 which is optimally visible within a dimmed room. The surgeon may then cut along the probe shaft 250 until light from the tip 204 is visible through tissue. It is desirable to make the probe 250 thin enough, for example 20 gauge, so that multiple passes through the breast 236 will not result in a hematoma. The rigid component of the probe 250 may be a hollow needle in which the optical fiber component may be secured by adhesive or other means. The probe tip 252 may be beveled flush with the needle tip.

In order to assess the integrity of the dual-hook optical localization fiber 200, a 2.27 kilogram (5 pound) weight was suspended from the fiber shaft 232 using a clamp while the dual hook assembly 202 was held firmly by a pair of needle nose pliers. There was no detachment of the dual hook assembly 202 from the tip portion 206. When the weight was increased to 3.41 kilograms (7.5 pounds), there was rapid detachment of the dual hook assembly 202 from the tip portion 206.

Measurement of the forces necessary to remove various types of hookwires completely from breast specimens was reported by Schoenberger S. G., et al. In a series of five tests for each of four types of hookwires (Homer, Percuguide, Kopans and Helix) the maximum force required of the twenty tests was 1220 grams for a Helix hookwire. The mean force required for hookwires was 274 grams, 585 grams, 454 grams, and 1004 grams, respectively. The force required to detach the dual hook assembly 202 from the tip portion 206 of the present invention exceeds that which is required to remove these hookwires completely from a breast 236. It may therefore be concluded that the dual-hook optical localization fiber may be constructed with sufficient strength for pre-operative localizations.

Quantitative torqued stress analysis was not performed on the fiber 200. It is possible that severe torquing of the dual hook assembly 202 may fragment the tip portion 206 if less than 2270 grams is applied. This test, however, does not replicate typical conditions in the clinical setting. In order to torque the dual hook assembly 202 while the hooks 224, 226 are engaged in tissue, a purposeful maneuver is necessary, one which the radiologist or surgeon would never need to perform.

If desired, the dual hook assembly 202 may be more firmly attached to the tip portion 206 by adding adhesive, or a thin synthetic or metal sleeve, coating, or coil encasing both the tip portion 206 and the proximal portion of the dual hook assembly 202 about the hole 214, or about both wires 212 to limit motion therebetween.

Figure 23:
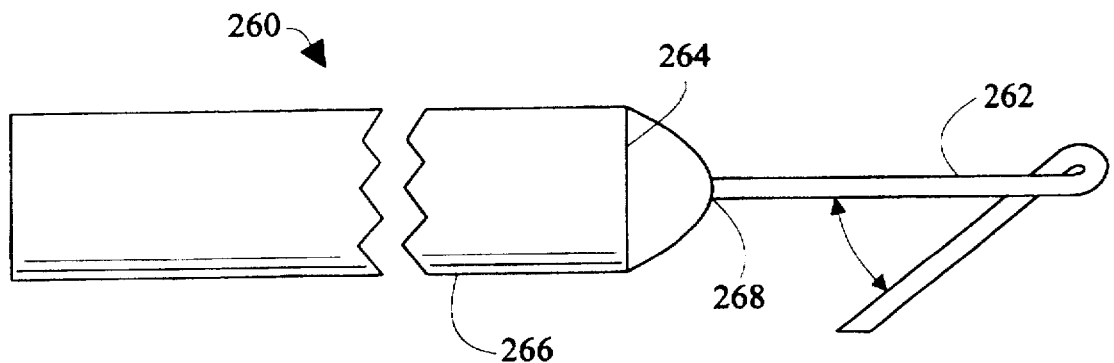
FIG. 23 is a side elevational view of a fused optical localization fiber.

FIG. 23 illustrates a fused optical localization fiber 260. A synthetic or metal hookwire 262 is fused to the tip 264 of the fiber 266 by the application of heat or a solvent to its base 268 and the tip to provide a means for retaining the tip proximate to a chosen location within tissue.

Figure 24:
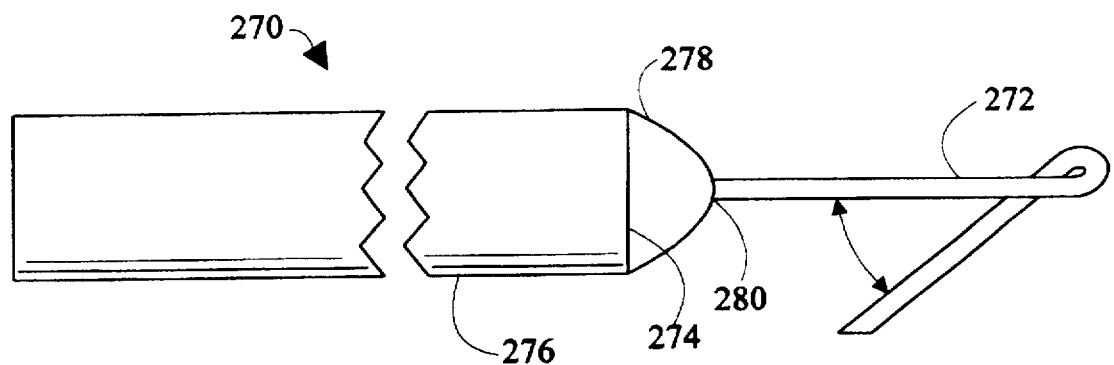
FIG. 24 is a side elevational view of a glued optical localization fiber.

FIG. 24 illustrates a glued optical localization fiber 270. The metallic or synthetic hook 272 is glued to the tip 274 of the fiber 276 by a glue, adhesive, or cement 278 at its base 280 to provide a means for retaining the tip proximate to a chosen location within tissue.

Figure 25:
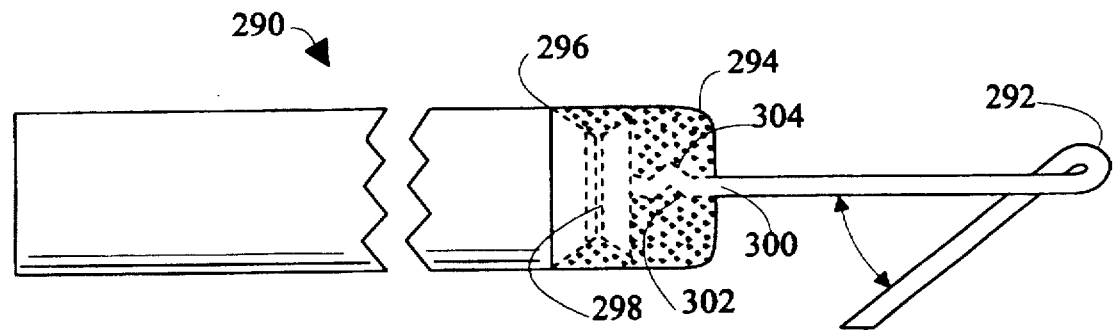
FIG. 25 is a side elevational view of a molded cap optical localization fiber.

FIGS. 25 illustrates a molded cap optical localization fiber 290 having hook 292, molded cap 294, and fiber tip 296 with bevel 298. The molded cap 294 retains the hook base 300 and is composed of plastic, epoxy, cement, or other rigid material. The hook base 300 has at least one bend 302. A second bend 304 facilitates retention within cap 294. Any surface irregularity or contour may be substituted for bevel 298. Any configuration of base 300 may be substituted. It should be clear that the embodiment illustrated in FIG. 25 is a specific example of the generic embodiment illustrated in FIG. 1.

Figure 26:
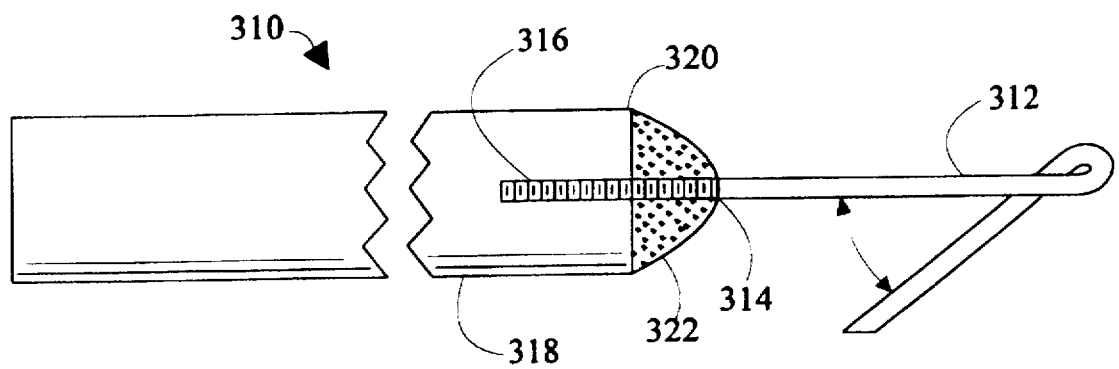
FIG. 26 is a side elevational view of a tapped optical localization fiber.

FIG. 26 illustrates a tapped optical localization fiber 310 having a hook 312. The hook base 314 has a screw portion 316 which is retained by tapped fiber tip portion 318. The tip 320 may be coated with cement 322 about hook base 314.

Figure 27:
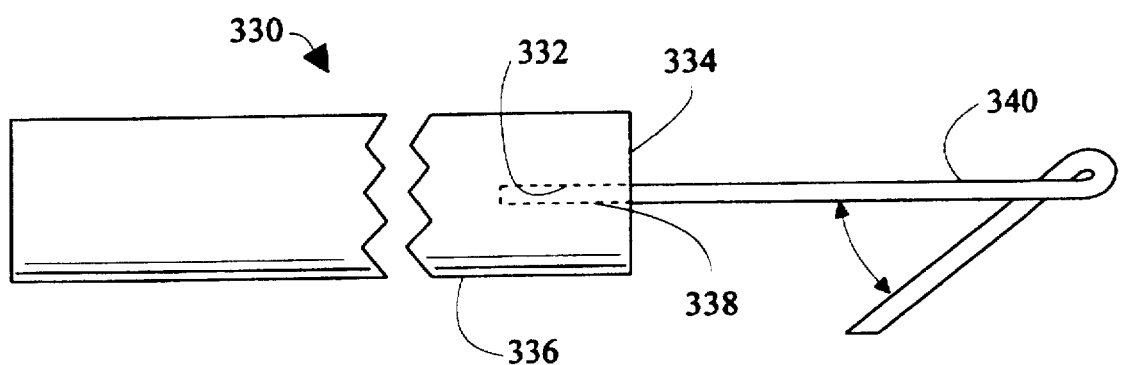
FIG. 27 is a side elevational view of an end drilled optical localization fiber.

FIG. 27 illustrates an end drilled optical localization fiber 330 similar to the fibers of FIGS. 23–26. A longitudinal hole 332 through the tip 334 into the tip portion 336 along the longitudinal axis of the fiber retains the base 338 of a metallic or synthetic hookwire 340 in the fiber by friction. Glue or cement may be used for retaining the base 338.

FIG. 28 is a side view illustrating a grooved optical localization fiber 350 in closed position. This embodiment is created by forming a longitudinal groove 352 in the outer surface 354 adjacent the tip 356 for carrying a hookwire 358 therein such that the cross section diameter 360 of the optical fiber shaft 362 and that of the optical fiber tip 356 along the entire length of the longitudinal groove 352 with indwelling hookwire 358 are approximately equal. The grooved optical localization fiber 350 may then be passed through a needle such as the needle 228 of FIGS. 20–22 having an internal diameter slightly greater than that of the optical fiber shaft 362. The hookwire 358 is anchored at the fiber tip 356 by a metallic or synthetic cap 364 or other substantially equivalent anchoring means.

FIG. 29 is a side view of the grooved optical localization fiber 350 in open position; this position occurs by a spring action of the hookwire 358 as the end 366 of the hookwire passes distal to the needle tip such as the needle tip 234 shown in FIG. 21.

FIG. 30 is a cross sectional view of the fiber 350 along the line 30—30 of FIG. 28 in the closed position, illustrating the groove 352 and indwelling hookwire 358. Note that the cross sectional diameter 368 with the hookwire 358 in the closed position is substantially equal to the diameter 360 of the shaft 362 in order to minimize the required needle gauge for passage of the grooved optical localization fiber 310 therethrough.

The combination of a laser or light source 240 (FIG. 22); an optical fiber; and means for retaining the tip of the optical fiber proximate to a chosen location within tissue comprises an optical localization fiber system. Sterile medical grade powdered carbon suspension in saline may also be a component of the system.

All fiber tips in all embodiments may be roughened to facilitate diffusion of light. This is especially advantageous if the fiber tip is covered distally; lateral roughening permits lateral light diffusion.

It should be noted that alternative methods of locating a hookwire tip within tissue may be implemented, however, they have disadvantages in comparison with optical localization fibers which would make them relatively less desirable for clinical use. For example, a metal detector may be used to determine the location of the metallic tip or hook of a synthetic localization wire. The tip of the wire may carry a radionuclide for detection by a Geiger counter. A piezoelectric crystal may be mounted on the tip of a hookwire in order to emit vibrations which could be detected by an ultrasonic probe. The tip of the hookwire could be heated above body temperature, and the position detected by thermography.

Optical fibers may consist of a bare silica, plastic or glass strand. This strand, or a bundle of strands may function as the core of a coated optical fiber. This coating may be formed from a variety of materials e.g. with silicate or doped silica cladding. Multiple coatings may be formed e.g. a buffer coating external to the cladding. The optical fiber may be designed for single or multiple laser wavelengths and differing peak optical power transmission capability. Numerous types of these optical fibers are available from 3M Corporation of Minneapolis, Minn.

Numerous types of lasers are available for linkage to these optical fibers including diode and Helium-Neon lasers particularly suited for use in the operating room environment. A 650–675 nanometer wavelength red beam laser operating at 1 to 20 milliwatts is easily seen through soft tissue. Other wavelengths and powers may be used, however.

In accordance with the features of the invention all fibers may be inserted through any needle similar in design to those currently employed for breast localization. All fibers may include glass, plastic, silicate or any material capable of electromagnetic wave transmission. All fiber tips may be fabricated of any synthetic, naturally occurring or metallic material, or any combination thereof. All fibers may be supplied with a diffuser tip formed from plastic, glass, quartz, sapphire or other translucent materials. All fibers may connect with a laser of an appropriate wavelength and power, a quartz-halogen light source, a high output light emitting diode, or any other type of light source deemed appropriate by those skilled in the art. All fibers may be linked to these light sources by various optical fiber connectors such as a ferrule connector or fiber adapter of a laser or other light source. All fibers may be clad or unclad with hard or soft cladding along all or any portion of their lengths. All fibers may have an external buffer coat. All fibers are sterilizable. All hooks have a spring action for easy passage through a localization needle and engagement into tissue as the localization needle is withdrawn. All embodiments may be used for pre-operative localization of tumors in other body parts such as lung, liver, and brain. All embodiments may be used for localizations guided by X-ray mammography, MRI, ultrasonography or nuclear medicine. All embodiments may be used in conjunction with apparatus for characterization of the optical properties of neoplasms.

To appraise the viability of the inventive concepts, both clad and coated and bare optical fiber tips were placed within chicken breast. Light from a 675 nanometer wavelength diode laser operating at 5 milliwatts was passed down each fiber. Although the amount of light radiating from the bare optical fiber tip decreased when the fiber was surrounded by moist tissue compared with air, the location of the tip of the fiber was well seen through several centimeters of tissue. The clad and coated fiber tips were more easily identified. Injection of carbon through a needle followed by illumination of the tissue by the fiber was performed. The carbon-marked region appeared dark, surrounded by illuminated tissue.

From the foregoing, it should now be recognized that optical localization fiber embodiments have been disclosed herein especially suited for preoperative localization of soft tissue lesions within breast, lung or brain, as well as for lesions within the retroperitoneal cavity and liver. These fibers may be positioned at a chosen location through medical instruments such as probes, cannulas or needles, using X-ray, magnetic resonance, computed tomography, ultrasound, or nuclear medicine guidance. The fibers are retained within the tissue by a variety of means disclosed herein.

Embodiments in accordance with the invention offer several potential advantages. The approximate location of the lesion may be determined by viewing the light radiating through tissue from the optical fiber tip. The surgeon operating on a localized breast may be able to approach the site of the lesion along the shortest route. This route does not necessarily have to be along the course of the localization wire. Because the site of the lesion can be determined through several centimeters of tissue, smaller dissections may be utilized thereby limiting the amount of cosmetic deformity resulting from a larger dissection. Because no manipulation of a hookwire is necessary either by pulling it or curving along it, the chance of displacement of the hook, and the chance of cutting through the wire are minimized. The continuous visualization of light emanating from the tip of the optical fiber provides the surgeon with continuous feedback, which is not practically obtained through intra-operative fluoroscopy or ultrasonography. Preferably, the operating suite is dimmed for optimal visualization of the light. Although the light may not be seen through skin, once the surgeon makes the skin incision, the light emanating from the fiber tip through tissue may be seen immediately, or after partial dissection.

Carbon marking of the lesion or lesion margin facilitates intra-operative localization and excision. The use of optical fibers for breast localization may permit characterization of the optical properties of breast tumors, if a receptive optical fiber is positioned at a chosen location proximate to the tumor and the transmitting optical fiber. In this manner, determination of malignancy versus benignancy is possible prior to engagement of the hook. In addition, carbon marking may be used to determine the presence or absence of the lesion in question within the surgically excised tissue. This is particularly useful if the lesion has been localized by magnetic resonance imaging, and the lesion is not visible on X-ray mammography, since radiographs of the excised specimen may be indeterminate.

The preferred embodiments of the invention described herein are exemplary and should not be construed as limitations on the scope of the invention. Any feature, shape, material composition or dimension of any embodiment may be readily combined, altered, or rearranged to achieve a substantially equivalent result, all of which are intended to be embraced within the scope of the appended claims.

What is claimed is:

1. An optical localization fiber, comprising:

an optical fiber having a tip and a tip portion adjacent said tip; and, means for retaining said tip proximate to a chosen location within tissue including said tip portion having a hole therethrough.

2. The optical localization fiber of claim 1 wherein said means for retaining further includes a wire having at least one hook and said wire passes through said hole.

3. The optical localization fiber of claim 2 wherein said at least one hook includes a first hook and a second hook.

4. The optical localization fiber of claim 3 wherein said wire has a first portion coupled to said first hook and a second portion coupled to said second hook and said first and second portions of said wire are substantially parallel to each other.

5. The optical localization fiber of claim 4 wherein said second hook is spaced further from said hole than said first hook.

6. The optical localization fiber of claim 5 wherein said optical fiber has a shaft with a circular cross section having a diameter and said tip portion has two substantially planar sides along said fiber from said hole to said tip, said two substantially planar sides substantially perpendicular to said hole and substantially parallel to each other, and each of said substantially planar sides spaced from said diameter a distance at least equal to the thickness of said wire such that the distance across said first and second portions of said wire and said tip portion is substantially equal to said diameter of said shaft.

* * * * *